US011707257B2

(12) United States Patent
Makita et al.

(10) Patent No.: US 11,707,257 B2
(45) Date of Patent: Jul. 25, 2023

(54) ULTRASONIC PROBE AND PROBE HEAD FOR ULTRASONIC PROBE

(71) Applicant: Canon Medical Systems Corporation, Otawara (JP)

(72) Inventors: Yasuhisa Makita, Nasushiobara (JP); Kengo Okada, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 540 days.

(21) Appl. No.: 16/446,666

(22) Filed: Jun. 20, 2019

(65) Prior Publication Data
US 2019/0307422 A1    Oct. 10, 2019

Related U.S. Application Data

(63) Continuation of application No. PCT/JP2019/005698, filed on Feb. 15, 2019.

(30) Foreign Application Priority Data

Feb. 15, 2018  (JP) ................................ 2018-025044

(51) Int. Cl.
*G10K 11/30* (2006.01)
*A61B 8/00* (2006.01)

(52) U.S. Cl.
CPC .......... *A61B 8/4281* (2013.01); *A61B 8/4444* (2013.01); *G10K 11/30* (2013.01)

(58) Field of Classification Search
CPC .......................... G10K 11/30; A61N 2007/006
See application file for complete search history.

(56) References Cited

U.S. PATENT DOCUMENTS

| 4,880,012 A | 11/1989 | Sato |
| 5,083,568 A * | 1/1992 | Shimazaki ............. G10K 11/30 600/459 |
| 5,577,507 A * | 11/1996 | Snyder ................. A61B 8/4281 600/472 |
| 2003/0076599 A1* | 4/2003 | Tarakci .................. G10K 11/30 359/642 |

(Continued)

FOREIGN PATENT DOCUMENTS

| JP | 61-118094 | 6/1986 |
| JP | 63-177700 | 7/1988 |

(Continued)

OTHER PUBLICATIONS

International Search Report dated May 7, 2019 in PCT/JP2019/005698, filed on Feb. 15, 2019 (with English translation of Categories of Cited Documents).

*Primary Examiner* — James M Kish
(74) *Attorney, Agent, or Firm* — Oblon, McClelland, Maier & Neustadt, L.L.P.

(57) ABSTRACT

The ultrasonic probe according to a present embodiment includes a piezoelectric vibrator and an acoustic lens. The piezoelectric vibrator is configured to transmit and receive an ultrasonic wave. The acoustic lens is provided on an ultrasonic-wave transmission/reception side. The acoustic lens is formed in such a manner that a surface shape of each of end regions located on both sides of a central region of a surface of the acoustic lens is formed to have a curvature different from a curvature of a surface shape of the central region of the surface of the acoustic lens.

12 Claims, 5 Drawing Sheets

(56) References Cited

U.S. PATENT DOCUMENTS

| | | | |
|---|---|---|---|
| 2011/0105900 A1* | 5/2011 | Entrekin | A61B 8/4455 |
| | | | 600/443 |
| 2013/0285174 A1 | 10/2013 | Sako et al. | |
| 2014/0005552 A1* | 1/2014 | Nishigaki | A61B 8/4444 |
| | | | 600/459 |
| 2014/0211587 A1* | 7/2014 | Kiyose | G01S 7/52053 |
| | | | 367/87 |
| 2016/0151044 A1* | 6/2016 | Kim | A61B 8/4455 |
| | | | 600/472 |
| 2017/0000459 A1 | 1/2017 | Shikata et al. | |
| 2018/0104384 A1* | 4/2018 | Nakai | C08G 77/80 |
| 2018/0146951 A1 | 5/2018 | Yoshida | |

FOREIGN PATENT DOCUMENTS

| | | |
|---|---|---|
| JP | 6-245931 | 9/1994 |
| JP | 9-37377 | 2/1997 |
| JP | 2000-201929 | 7/2000 |
| JP | 2004-248860 | 9/2004 |
| JP | 2012-100994 | 5/2012 |
| JP | 2015-221214 | 12/2015 |
| WO | WO 2016/208631 A1 | 12/2016 |

\* cited by examiner

ULTRASONIC PROBE AND PROBE HEAD FOR ULTRASONIC PROBE

CROSS-REFERENCE TO RELATED APPLICATION

This application is a Continuation Application of No. PCT/JP2019/005698, filed on Feb. 15, 2019, and the PCT application is based upon and claims the benefit of priority from Japanese Patent Application No. 2018-025044, filed on Feb. 15, 2018, the entire contents of which are incorporated herein by reference.

FIELD

An embodiment as an aspect of the present invention relates to an ultrasonic probe and a probe head for an ultrasonic probe.

BACKGROUND

Generally, when an ultrasonic scan is performed while an ultrasonic probe for transmitting and receiving ultrasonic waves is in contact with a living body, an acoustic coupling agent is applied to the contact surface of the acoustic lens with the living body. This is to ensure that there is no air layer between the acoustic lens placed at a tip of the ultrasonic probe and the surface of the living body. The acoustic coupling agent is also called an echo jelly.

When the ultrasonic probe is used by an operator for a long time while being moved on the surface of the living body, the amount of the echo jelly decreases from the lens surface of the ultrasonic probe and the surface of the living body, and consequently, an air layer intervenes between the acoustic lens and the surface of the living body in some cases. When an ultrasonic wave is transmitted to the air portion, the ultrasonic wave is totally reflected at the air portion without reaching the living body and the reflection echo from the living body cannot be acquired. In this case, there occurs a phenomenon in which positional information corresponding to the air portion in the ultrasonic image cannot be acquired and this portion is depicted as a decolorized black area in the ultrasound image.

DETAILED DESCRIPTION

An ultrasonic probe and a probe head for an ultrasonic probe according to a present embodiment will be described with reference to the accompanying drawings.

The ultrasonic probe according to a present embodiment includes a piezoelectric vibrator and an acoustic lens. The piezoelectric vibrator is configured to transmit and receive an ultrasonic wave. The acoustic lens is provided on an ultrasonic-wave transmission/reception side. The acoustic lens is formed in such a manner that a surface shape of each of end regions located on both sides of a central region of a surface of the acoustic lens is formed to have a curvature different from a curvature of a surface shape of the central region of the surface of the acoustic lens.

Figure 1:
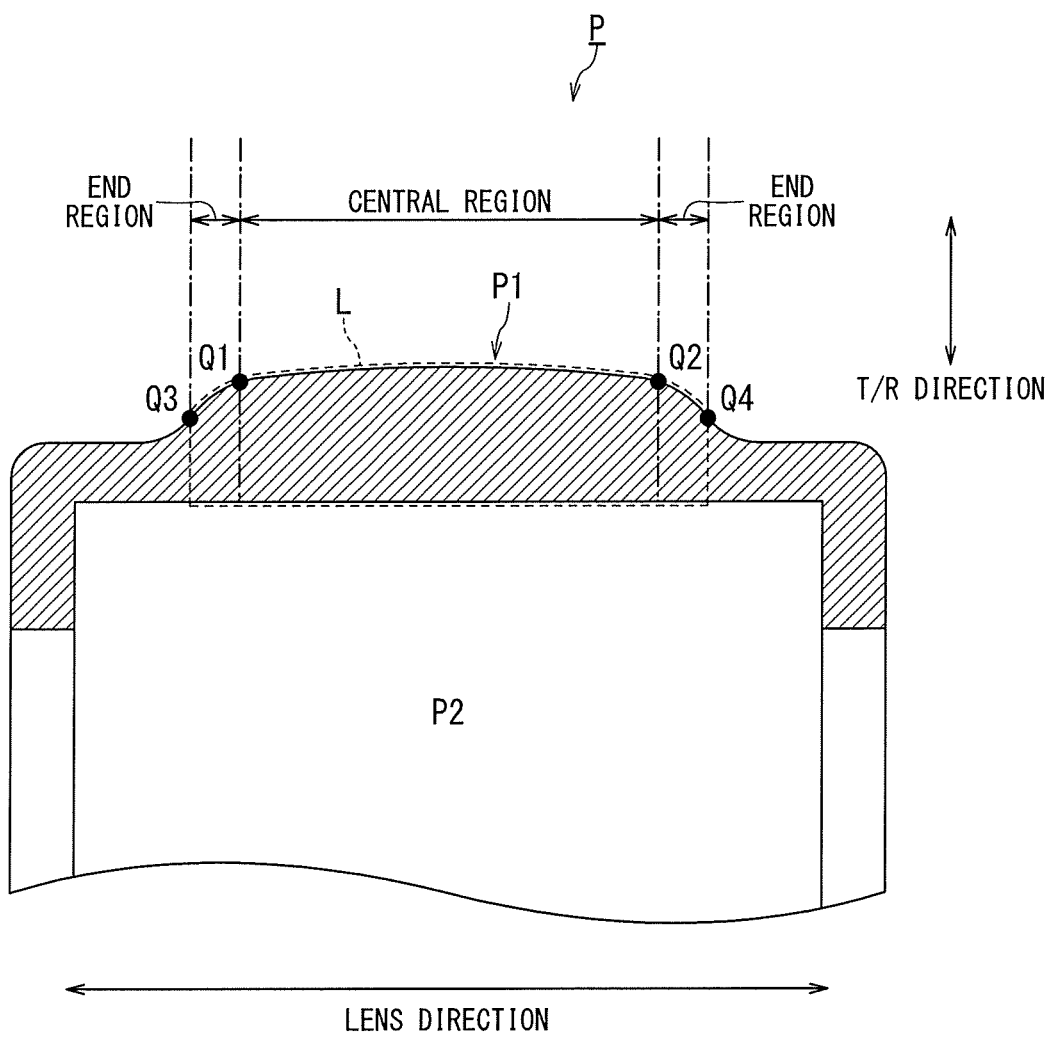
FIG. 1 is a longitudinal cross-sectional view illustrating a concept of a configuration of an ultrasonic probe according to a present embodiment.

FIG. 1 is a longitudinal cross-sectional view illustrating the concept of the configuration of the ultrasonic probe according to a present embodiment.

FIG. 1 shows an ultrasonic probe P according to the present embodiment. The ultrasonic probe P includes a probe head P1 (a hatched region of FIG. 1) for the ultrasonic probe P including a unit such as an acoustic lens L, and a probe body P2 (the remaining region of the ultrasonic probe P excluding the hatched region). The probe head P1 is not limited to the hatched region. The probe head P1 may be provided with other members such as a piezoelectric vibrator 11, an acoustic matching layer 13 and a backing material 14 which will be described later in addition to the acoustic lens L, but the illustration thereof is omitted for convenience of explanation. FIG. 1 shows a longitudinal cross-section formed by a lens direction of the ultrasonic probe P and a transmitting and receiving (T/R) direction of ultrasonic waves. The lens direction is also called an elevation direction, and the T/R direction is also called a depth direction.

The acoustic lens L of the probe head P1 is provided on the transmission/reception side of the ultrasonic wave. In the surface of the acoustic lens L (i.e., the surface to be brought into contact with the surface of the living body), each of the two end regions positioned on both sides of the central region is formed into a surface shape that has a curvature different from the curvature of the surface shape of the central region. For instance, when the acoustic lens L is divided into the central region and the end regions in the lens direction, the portion located as a surface portion of the end region between the changing points Q1 and Q3 has a shape with a certain curvature. The surface shape between the changing points Q1 and Q3 of one end region is formed into a shape with a curvature that is different from the curvature of the surface shape of the central region between the changing points Q1 and Q2. The surface shape between the changing points Q2 and Q4 in the opposite end region is similar to the surface shape between the changing points Q1 and Q3 in the one end region.

In the present specification, the surface shape of the central region is not limited to the case of a circular arc. The surface shape of the central region includes the case where the surface shape is flat, that is, the case where the curvature is infinite.

In view of providing a stepped portion for retaining the echo jelly, it is preferable that a part of the surface of each end region is formed into a shape having a curvature smaller than the curvature of the surface shape of the central region. However, this is not an indispensable condition. In other words, the portion between the changing points Q3 and Q1 (the same applies between the changing points Q4 and Q2) of the surface of the end region preferably has a curvature smaller than the curvature between the changing points Q1 and Q2. In this case, the portion of the end region is formed to be continuous to the surface of the central region (between the end regions) via the changing points Q1 and Q2.

In view of providing the stepped portion for retaining the echo jelly, this portion of each end region preferably has an inflection point on the other side with respect to the side that is continuous to the surface of the central region, in the longitudinal cross-section. However, this is not an indispensable condition. That is, it is preferable that the changing points Q3 and Q4 are inflection points. The inflection point means a point where the bending direction changes.

Since the acoustic lens L has the above-described configuration, the echo jelly can be stably supplied between the surface of the living body and the probe surface for transmitting/receiving ultrasonic waves when an operator moves the ultrasonic probe P in the lens direction. According to the above-described configuration, it is possible to reduce generation of a decolorized black area due to the intervention of air, in an ultrasonic image as described below.

Although a description has been given of the case where the ultrasonic probe P is divided into the central region and the end regions in the lens direction in FIG. 1, it is not limited to such a case. For instance, the ultrasonic probe P may be divided into the central region and the end regions in the array direction. In this case, when an operator moves the ultrasonic probe P in the array direction, the echo jelly can be stably supplied between the surface of the living body and the probe surface for transmitting/receiving ultrasonic waves. The array direction is also called an azimuth direction.

For instance, the ultrasonic probe P may be divided into the central region and the end regions in the lens direction and in the array direction. In this case, when an operator moves the ultrasonic probe P in the lens direction or in the array direction, echo jelly can be stably supplied between the surface of the living body and the probe surface for transmitting/receiving ultrasonic waves. Unless otherwise specifically noted, hereinafter, a description will be given of the case where the ultrasonic probe P is divided into the central region and the end regions in the lens direction.

Hereinafter, as one aspect of the ultrasonic probe P, a description will be given of an ultrasonic probe 10 in which only the central region serves as an acoustically effective portion. However, the ultrasonic probe P is not limited to the case of such an ultrasonic probe 10. For instance, the entirety of the acoustically effective portion and a part inside each acoustically ineffective portion may be configured as the central region while only a part of the outside of each acoustically ineffective portion is being configured as each end region. Additionally or alternatively, only a part of the center of the acoustically effective portion may be configured as the central region. It should be noted that the acoustically effective portion means a portion that is a part of the center in the acoustic lens L region and that corresponds to the path of the ultrasonic wave transmitted and received by the piezoelectric vibrator. The acoustically ineffective portion means a region that includes a part of the outside of the acoustic lens L region and does not collide with the path of the ultrasonic wave transmitted and received by the piezoelectric vibrator.

Next, a description will be given of the case where the ultrasonic probe P is the ultrasonic probe 10 by referring to FIGS. 2 to 5B.

Figure 2:
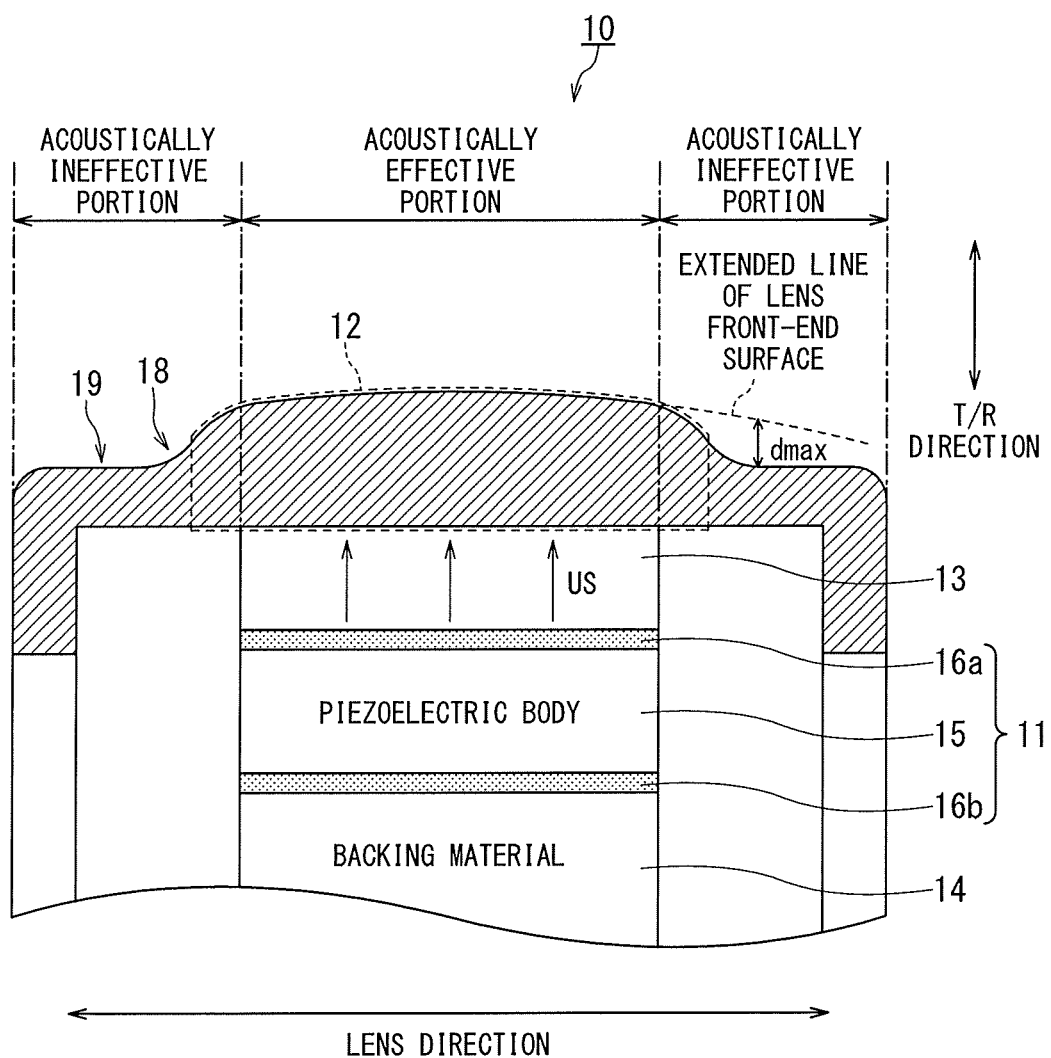
FIG. 2 is a longitudinal cross-sectional view illustrating a configuration of the ultrasonic probe according to the present embodiment.

FIG. 2 is a longitudinal cross-sectional view illustrating a configuration of the ultrasonic probe according to the present embodiment.

FIG. 2 illustrates the ultrasonic probe 10 according to the present embodiment. The ultrasonic probe 10 includes at least piezoelectric vibrators 11, an acoustic lens 12 (convex portion) as an example of the acoustic lens L, an acoustic matching layer 13, and a backing material 14. The piezoelectric vibrators 11, the acoustic lens 12, the acoustic matching layer 13 and the backing material 14 may be included in the probe head P1 shown in FIG. 1 or in the probe body P2 shown in FIG. 1. The ultrasonic probe 10 may include other components, and illustration of the other components is omitted for avoiding complication of the description. FIG. 2 shows a longitudinal cross-section formed by the T/R direction and the lens direction (i.e., elevation direction) of the ultrasonic probe 10.

The ultrasonic probe 10 can be classified into various types such as a linear type, a convex type, and a sector type depending on difference in scanning method. In addition, the ultrasonic probe 10 includes various probes classified by a difference in array arrangement dimension such as a one-dimensional (1D) array probe and a two-dimensional (2D) array probe. In the 1D array probe, plural piezoelectric vibrators are one-dimensionally arranged in the array direction, i.e., in the azimuth direction that is orthogonal to the lens direction. In the 2D array probe, plural piezoelectric vibrators are two-dimensionally arrayed in the array direction and in the lens direction. Furthermore, as another configuration example, the ultrasonic probe 10 has a mechanism for mechanically swinging one element or 1D array probe in the elevation direction, and configured to acquire a three-dimensional image (also called as a "mechanical 4D probe"). The 1D array probe also includes an ultrasonic probe in which a small number of piezoelectric vibrators are arrayed in the lens direction. Although the 1D array probe will be described as one aspect of the ultrasonic probe 10 in the following description, embodiments of the present invention are not limited to such an aspect.

Each piezoelectric vibrator 11 is an ultrasonic transducer that transmits the generated ultrasonic waves to the outside and receives the ultrasonic waves from the outside. Each piezoelectric vibrator 11 includes a piezoelectric body 15, a front-surface electrode 16a, and a back-surface electrode 16b.

The front-surface electrode 16a is disposed on the lens-side surface of the piezoelectric body 15 and the back-surface electrode 16b is disposed on the opposite surface such that the piezoelectric body 15 is sandwiched between the two electrodes 16a and 16b.

Each piezoelectric vibrator 11 transmits and receives an ultrasonic wave at the portion where the two electrodes, i.e., the front-surface electrode 16a and the back-surface electrode 16b face each other. Specifically, out of the surfaces of the front-surface electrode 16a, the surface facing the back-surface electrode 16b is hereinafter referred to as a transmission/reception surface. An ultrasonic wave generated in the piezoelectric body 15 is radiated from the transmission/reception surface. Upon receiving an ultrasonic wave from the outside of the probe, the ultrasonic wave is received on the transmission/reception surface.

The acoustic lens 12 is a lens that converges ultrasonic waves transmitted and received by each piezoelectric vibrator 11. The acoustic lens 12 serves as a contact surface with the living body during ultrasonic scanning.

The surface of the ultrasonic probe 10 is divided into an acoustically effective portion and two acoustically ineffective portions depending on the transmission/reception region of the ultrasonic wave in each piezoelectric vibrator 11. The acoustically effective portion is a region for transmitting and receiving ultrasonic waves, and the acoustically ineffective portions are respective regions that are positioned on both sides of the acoustically effective portion and do not transmit or receive ultrasonic waves. That is, the acoustically effective portion and the acoustically ineffective portions are determined by the transmission/reception region of the ultrasonic wave in each piezoelectric vibrator 11.

As shown in FIG. 2, the width of the acoustically effective portion of the acoustic lens 12 may be the same as the width of the transmission/reception surface of the front-surface electrode 16a. Additionally or alternatively, the width of the acoustically effective portion of the acoustic lens 12 may be wider than the width of the transmission/reception surface of the front-surface electrode 16a. Each acoustically ineffective portion is a region outside the end of the acoustic effective portion.

The acoustically effective portion of the acoustic lens 12 includes a convex surface having a curvature. The acoustically ineffective portions are formed so as to be lower than the lens front-end surface of the acoustic lens 12, i.e., the extended line of the convex surface, so that a stepped portion is formed between the acoustically effective portion and each acoustically ineffective portion. In FIG. 2, the maximum height difference between the extended line of the lens front-end surface and the surface of the shoulder portion 19 in each acoustically ineffective portion is defined as a level difference "dmax".

Each acoustically ineffective portion includes a concave portion 18 having an arbitrary curvature at the portion that is formed to be lower than the extended line of the lens front-end surface (i.e., convex surface). That is, the curvature of the surface of the ultrasonic probe 10 changes from convex to concave in each acoustically ineffective portion. In each acoustically ineffective portion, the flat shoulder portion 19 is formed from the concave portion 18 to the lens end.

Since the stepped portion is provided between the surface of each acoustically ineffective portion and the surface of the acoustically effective portion, a certain space is generated between the extended line of the lens front-end surface and the lens surface in the surface of each acoustically ineffective portion. This space serves as the region for retaining echo jelly when the echo jelly is applied to the surface of the living body and then ultrasonic scanning is performed while moving the ultrasonic probe 10 on the surface of the living body. Each region for retaining the echo jelly can be made larger by forming the concave portion 18 in each acoustically ineffective portion.

In each acoustically ineffective portion, the stepped portion formed to be lower than the extended line of the lens front-end surface may be formed in the lens direction as in the embodiment shown in FIG. 2 or may be formed in the array direction. In each acoustically ineffective portion, the stepped portion may be formed in both of the array direction and the lens direction.

For instance, silicone rubber, polymethylpentene, or butadiene rubber may be used for the material of the acoustically effective portion and the acoustically ineffective portions.

The acoustic matching layer 13 is provided between each piezoelectric vibrator 11 and the acoustic lens 12 and is made of a substance having an intermediate acoustic impedance between each piezoelectric vibrator 11 and the living body. Since the difference in acoustic impedance between each piezoelectric vibrator 11 and the living body becomes smaller by providing the acoustic matching layer 13, ultrasonic waves can be efficiently transmitted to the living body.

The backing material 14 is a member provided on the back surface of each piezoelectric vibrator 11 for suppressing vibration. Since the sound in the direction opposite to the radiation direction of the ultrasonic wave is absorbed by providing the backing material 14 and thereby extra vibration is suppressed, the pulse width of the ultrasonic wave can be reduced.

Next, a description will be given of the decolorized black area in an ultrasonic image by referring to FIGS. 5A and 5B.

Figure 5A:
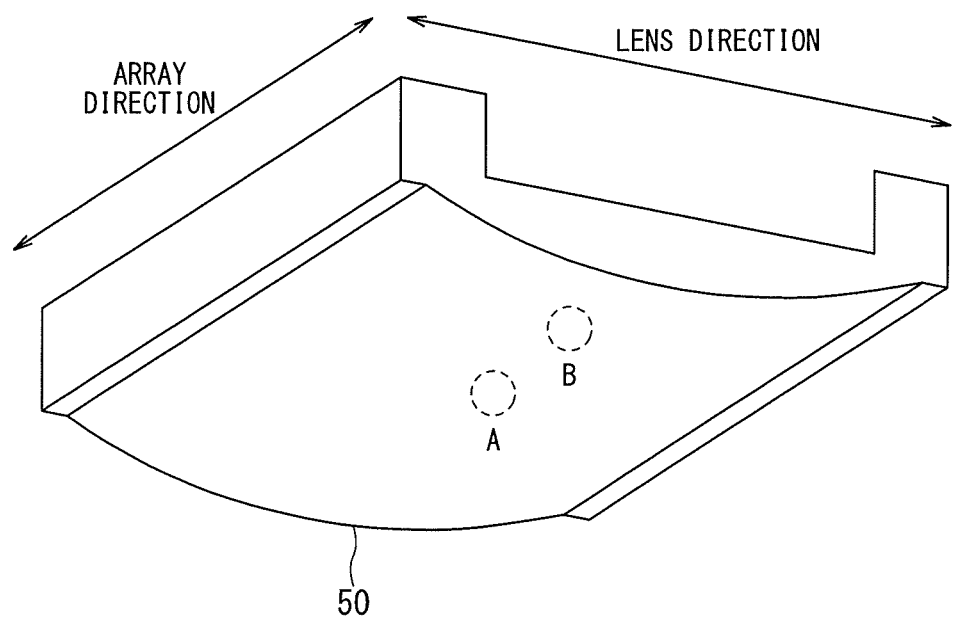
FIG. 5A is a perspective view illustrating a comparative example of an acoustic lens.

FIG. 5A is a perspective view illustrating a comparative example of an acoustic lens. In FIG. 5A, the structure of the other probe components such as piezoelectric vibrators is omitted.

FIG. 5A shows an acoustic lens 50 according to the comparative example. In the acoustic lens 50, a convex portion having a curvature is formed in the lens direction. Both sides of the acoustic lens 50 are flatly formed from each end of the convex surface to the lens end. The respective positions A and B on the convex surface of the lens indicate the transmission positions of the ultrasonic wave.

When an operator applies echo jelly to the living body and then performs ultrasonic scanning while moving the ultrasonic probe by using this acoustic lens 50 as a contact surface, the echo jelly on the surface of the living body is directly supplied to the convex surface of the lens for transmitting/receiving ultrasonic waves. When the ultrasonic scanning is performed by using the acoustic lens 50 of such a configuration for a long time and the amount of the echo jelly on the surface of the living body is reduced, there is a possibility that an air layer intervenes around the convex surface of the lens. In addition, air bubbles are mixed in the echo jelly in some cases, and thus the echo jelly containing air bubbles is supplied around the convex surface of the lens in some cases.

When an air layer intervenes between the ultrasonic probe and the surface of the living body, an ultrasonic wave transmitted from the convex surface of the lens is strongly reflected at the air portion, and consequently, the ultrasonic wave does not reach the surface of the living body and a reflected echo cannot be received.

Figure 5B:
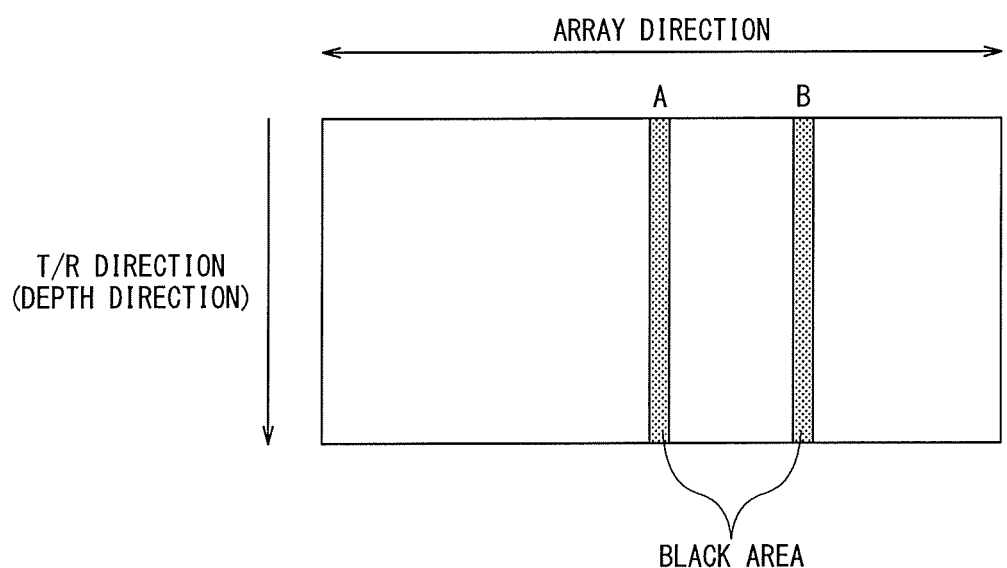
FIG. 5B is a schematic diagram illustrating one case of an ultrasonic image acquired as a result of using the acoustic lens shown in FIG. 5A.

FIG. 5B is a schematic diagram illustrating one case of an ultrasonic image acquired as a result of using the acoustic lens 50 shown in FIG. 5A. The horizontal axis indicates the transmission position of the ultrasonic wave, and the vertical axis indicates the depth from the surface of the living body.

As shown in FIG. 5B, when the ultrasonic wave transmitted from the convex surface of the acoustic lens 50 is reflected by the air layer, the reflected echo cannot be received and the ultrasonic image includes the above-described black area. In the ultrasonic image shown in FIG. 5B, it is shown that the ultrasonic waves transmitted from the respective transmission positions A and B are reflected by the air layer and are depicted as the black areas. The longer the time of performing the ultrasonic scanning becomes, the higher the probability of the generation of the black area in the ultrasonic image becomes.

Next, the operation of the ultrasonic probe 10 according to the embodiment will be described in detail.

Figure 3A:
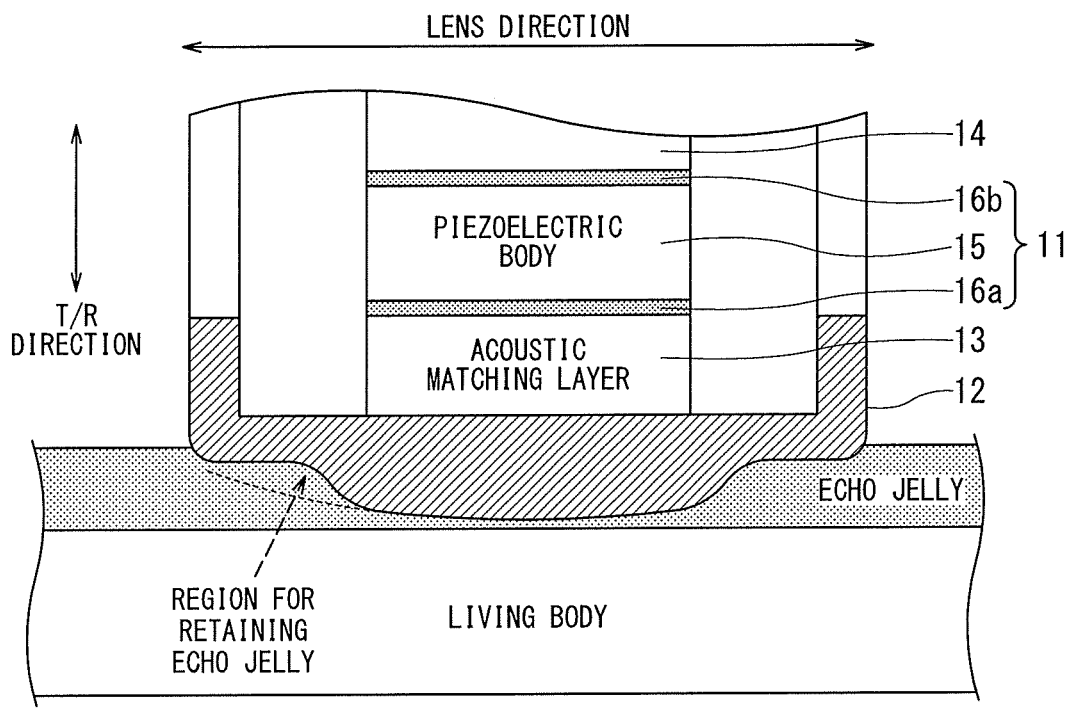
FIG. 3A is a schematic diagram illustrating a state in which an echo jelly is applied to a surface of a living body and the ultrasonic probe according to the present embodiment is placed on the surface of the living body.

FIG. 3A is a schematic diagram illustrating a state in which an echo jelly is applied to the surface of the living body and the ultrasonic probe 10 is placed on the surface of the living body.

The stepped portion provided in each acoustically ineffective portion (i.e., fixed space between the extended line of the lens front-end surface and the lens surface of each acoustically ineffective portion) serves as a region for retaining the echo jelly. Further, since the concave portion is provided in each acoustically ineffective portion, more echo jelly is retained in each acoustically ineffective portion.

Figure 3B:
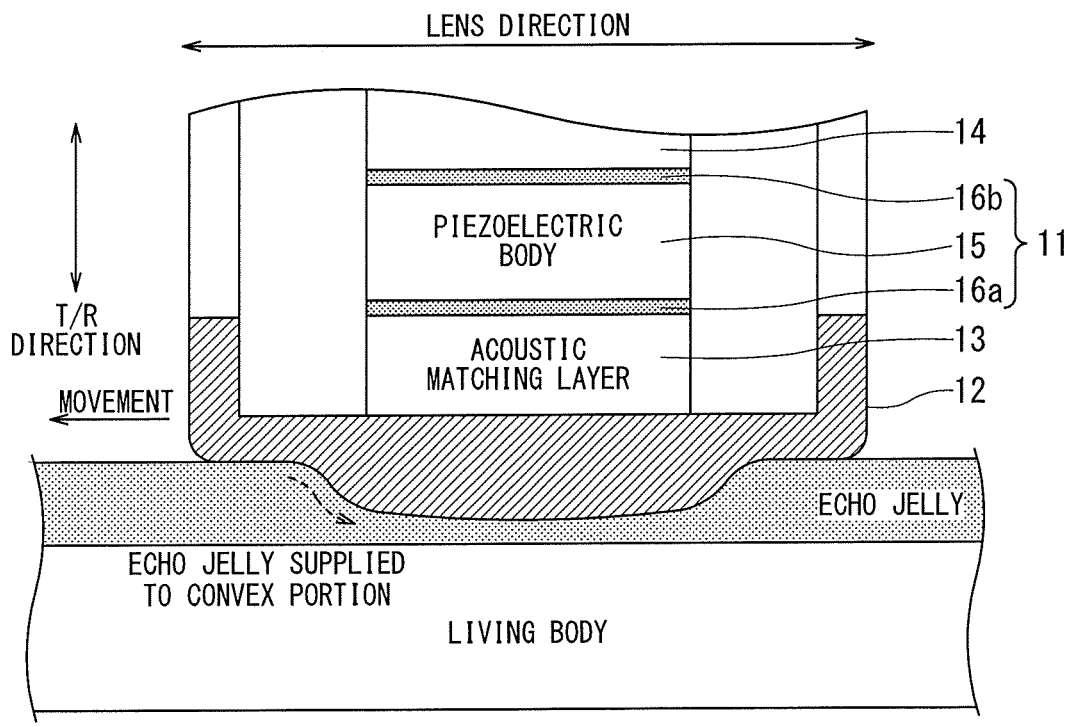
FIG. 3B is a schematic diagram illustrating a state in which the ultrasonic probe according to the present embodiment is moved on the surface of the living body.

FIG. 3B is a schematic diagram illustrating a state in which the ultrasonic probe 10 is moved on the surface of the living body.

The echo jelly retained in the stepped portion provided in each acoustically ineffective portion of the acoustic lens 12 is supplied to the lens front-end surface of the acoustically effective portion according to the movement of the ultrasonic probe 10.

Since the concave portion is provided in each acoustically ineffective portion, more echo jelly is retained. Thus, even when air bubbles are contained in the echo jelly, the air bubbles in the echo jelly remain in the stepped portion of each acoustically ineffective portion, and thereby the air bubbles are suppressed or prevented from moving to the lens front-end surface of the acoustically effective portion.

As described above, the stepped portion for retaining the echo jelly is provided in each acoustically ineffective portion, and thereby the echo jelly is supplied to the lens front-end surface of the acoustically effective portion through the stepped portion. Accordingly, even when ultrasonic scanning is performed for a long time and the amount of the echo jelly on the surface of the living body is reduced, the echo jelly can be stably supplied between the lens front-end surface of the ultrasonic probe 10 and the surface of the living body. As a result, intervening of an air layer on the lens surface is suppressed, so that generation of the black area in the ultrasonic image can be reduced and diagnostic accuracy can be improved.

In the case of the ultrasonic probe in which the acoustic lens 50 of the comparative example shown in FIG. 5A is used, in order to prevent generation of the black area in the ultrasonic image, the operator is required to add the echo jelly on the surface of the living body each time the amount of the echo jelly is reduced. However, according to the ultrasonic probe 10, the stepped portion for retaining the echo jelly is provided in each acoustically ineffective portion, and thus it is possible to continue the ultrasonic scan and to reduce the burden on the operator.

In the ultrasonic probe 10, the maximum value dmax (shown in FIG. 2) and/or the level difference "d" (shown in FIG. 4) of the stepped portion of each acoustically ineffective portion is desirably 0.2 mm or more. The magnitude of the level difference of each acoustically ineffective portion shown in FIG. 2 varies according to the lens direction. The optimum value of the maximum value dmax of the stepped portion of each acoustically ineffective portion varies depending on the design parameters such as the width of the entire ultrasonic probe 10 in the lens direction. Although the maximum value dmax of the stepped portion of each acoustically ineffective portion will be described below, the same applies to the level difference "d" of the acoustically ineffective portion.

In view of enlarging the region for retaining the echo jelly in each acoustically ineffective portion, the probe is preferably formed such that the maximum value dmax of the stepped portion becomes larger. However, when the maximum value dmax of the stepped portion is made larger, each acoustically effective portion is required to be formed more thickly by the increment of the maximum value dmax, which may affect the characteristics of the ultrasonic wave to be transmitted.

Additionally, depending on the frequency of ultrasonic waves to be transmitted and received, the optimum effective thickness of the acoustic effective portion varies. For instance, in the case of a small frequency such as several hundred kHz, the influence of the attenuation at the acoustically effective portion is small, and thus the maximum value dmax of each stepped portion can be set to a large value (e.g., the maximum value dmax of the stepped portion can be 0.7 mm or more). Contrastively, in the case of a large frequency such as several MHz, the maximum value dmax of each stepped portion is required to be set as a small value (e.g., dmax is 0.2 to 0.7 mm) in consideration of the attenuation of the ultrasonic wave in the acoustically effective portion. Thus, the maximum value dmax of the stepped portion in each acoustically ineffective portion is set to an optimum value in consideration of, e.g., characteristics of the ultrasonic wave.

As a material of the acoustically effective portion and the acoustically ineffective portions, it is possible to use a hydrophobic material, e.g., a material that has a contact angle with respect to water of 60° or more. When a hydrophobic material is used, a phenomenon of repelling the echo jelly on the surface of the acoustically effective portion and the acoustically ineffective portions occurs, and there is a possibility that the time until disappearance of the echo jelly is shortened. When the maximum value dmax of the stepped portion in the surface of each acoustically ineffective portion is set in the same manner as the present embodiment, the echo jelly can be stably supplied to the lens front-end surface that is the acoustically effective portion, and thus a hydrophobic material can be used as the acoustically effective portion and the acoustically ineffective portions.

Figure 4:
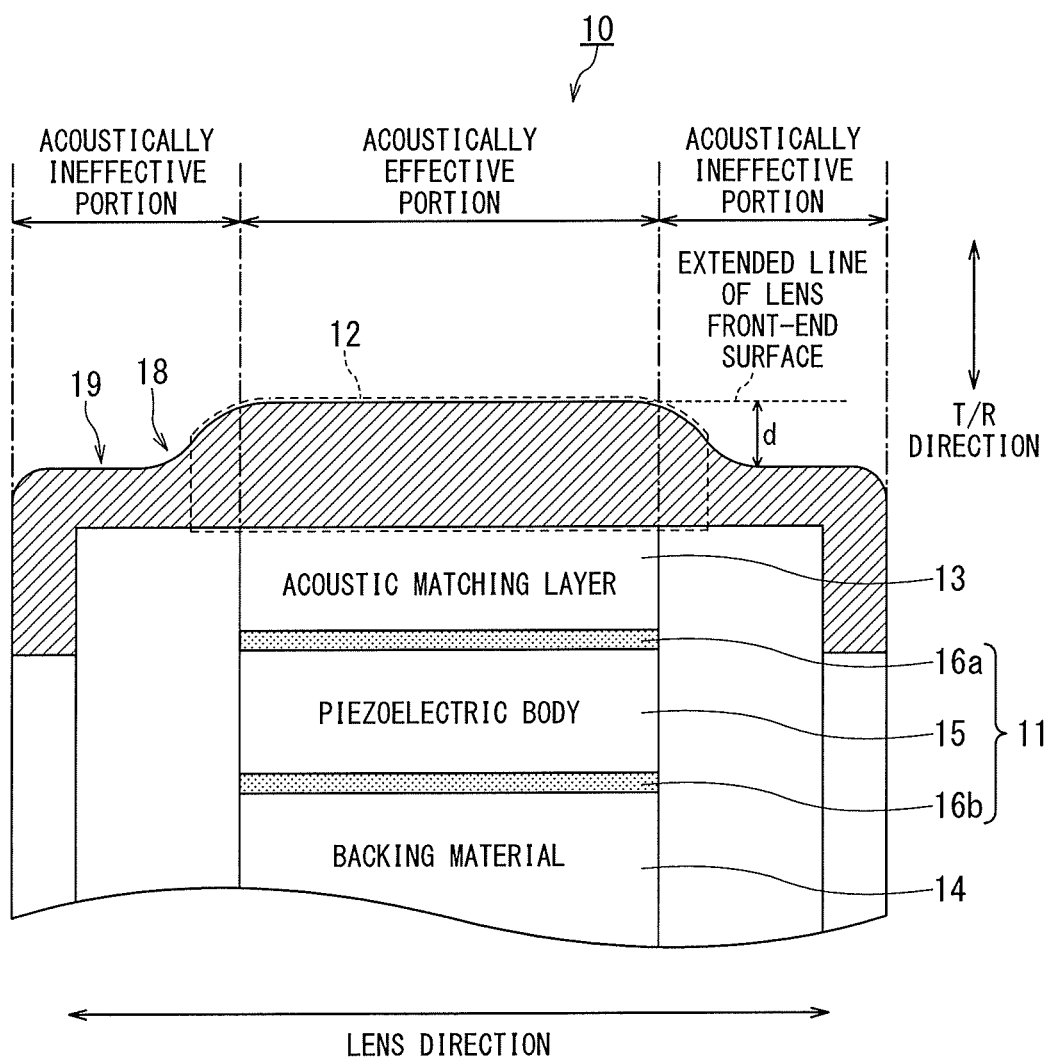
FIG. 4 is a longitudinal cross-sectional view illustrating another configuration of the ultrasonic probe according to the present embodiment.

FIG. 4 is a longitudinal cross-sectional view illustrating another configuration of the ultrasonic probe 10 according to the embodiment. In FIG. 4, the same components as those shown in FIG. 2 are denoted by the same reference signs, and duplicate description is omitted.

In the acoustic lens 12 shown in FIG. 2, the lens front-end surface of the acoustically effective portion is formed as a convex surface having a curvature. In the configuration, the lens front-end surface of the acoustically effective portion of the acoustic lens 12 is formed to have a flat portion that is substantially parallel to the ultrasonic-wave transmission/reception surface of each piezoelectric vibrator 11.

An outer surface of each acoustically ineffective portion is formed to have the shoulder portion 19 that is formed to be parallel to the flat portion of the acoustically effective portion.

Depending on conditions such as the size of the ultrasonic probe 10 and the inspection target part, the shape of the lens is changed. For instance, a lens in which the lens front-end surface has a curvature and another lens in which the lens front-end surface is flat may be used. Even when the lens front-end surface is flat, echo jelly can be stably supplied to the lens front-end surface of the acoustically effective portion by providing the step portion for retaining the echo jelly in each acoustically ineffective portion. Thus, even in such a case, intervening of an air layer on the lens surface is suppressed, and consequently, it is possible to reduce generation of the black area in the ultrasonic image.

According to at least one of the embodiments described above, it is possible to stably supply an echo jelly between an acoustic lens which transmits and receives the ultrasonic waves and the surface of the living body. As a result, it is possible to reduce the occurrence of the decolorized black area on the ultrasonic image due to the presence of air. While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An ultrasonic probe comprising:
a piezoelectric vibrator configured to transmit and receive an ultrasonic wave; and
an acoustic lens provided on an ultrasonic-wave transmission side of the piezoelectric vibrator, the acoustic lens including an acoustically effective portion which is a region corresponding to a path of the ultrasonic wave, and including acoustically ineffective portions which are regions not corresponding to the path of the ultrasonic wave, wherein
each of the acoustically ineffective portions includes a stepped portion in end regions adjacent to the acoustically effective portion, the stepped portion being formed such that the acoustically effective portion protrudes in a transmission direction of the ultrasonic wave more than the acoustically ineffective portions.

2. The ultrasonic probe according to claim 1, wherein each of the stepped portions is configured to retain an echo jelly applied to the subject.

3. The ultrasonic probe according to claim 1, wherein each of the acoustically ineffective portions has a portion existing at a location extending from an extended line of a surface of the acoustically effective portion toward the piezoelectric vibrator.

4. The ultrasonic probe according to claim 3, wherein each of the acoustically ineffective portions includes a concave having a portion existing at a location extending from an extended line of a surface of the acoustically effective portion toward the piezoelectric vibrator.

5. The ultrasonic probe according to claim 1, wherein each of the acoustically ineffective portions has a portion existing at a location extending from an extended line of a surface of the acoustically effective portion toward the piezoelectric vibrator by 0.2 mm or more.

6. The ultrasonic probe according to claim 1, wherein a material of the acoustically effective portion and the acoustically ineffective portions is any one of polymethylpentene, silicone rubber, and butadiene rubber.

7. The ultrasonic probe according to claim 1, wherein the acoustically effective portion and the acoustically ineffective portions are formed of a material that has a contact angle with respect to water of 60° or more.

8. The ultrasonic probe according to claim 1, wherein
the acoustic lens has a first convex surface with a first end and a second end,
the first one of the end regions has a second convex surface immediately adjacent to and continuous with the first end of the central region,
the second one of the end regions has a third convex surface immediately adjacent to and continuous with the second end of the central region, and
a curvature of the second and third convex surfaces are each smaller than a curvature of the first convex surface.

9. The ultrasonic probe according to claim 8, wherein
the second convex surface extends from the first end to a first inflection,
the third convex surface extends from the second end to a second inflection point,
the acoustically ineffective portion has a flat portion that is substantially parallel to a transmission/reception surface of the ultrasonic wave,
a first concave surface extends between the first inflection point and the flat portion, and
a second concave surface extends between the second inflection point and the flat portion.

10. The ultrasonic probe according to claim 1, wherein
the acoustically effective portion is provided in a central region of the acoustic lens, and
a surface shape of each of the end regions of the acoustically ineffective portions is formed with a different curvature than the surface shape of the central region.

11. A probe head for an ultrasonic probe comprising:
an acoustic lens provided on an ultrasonic-wave transmission side of a piezoelectric vibrator, the acoustic lens including an acoustically effective portion which is a region corresponding to a path of the ultrasonic wave, and including acoustically ineffective portions which are regions not corresponding to the path of the ultrasonic wave, wherein
each of the acoustically ineffective portions includes a stepped portion in end regions adjacent to the acoustically effective portion, the stepped portion being formed such that the acoustically effective portion protrudes in a transmission direction of the ultrasonic wave more than the acoustically ineffective portions.

12. The probe head according to claim 11, further comprising:
the piezoelectric vibrator being configured to transmit and receive the ultrasonic wave.

* * * * *